United States Patent [19]

Szabo

[11] Patent Number: 5,325,846
[45] Date of Patent: Jul. 5, 1994

[54] ENDOSCOPIC DRAPING APPARATUS AND METHOD

[75] Inventor: Steve Szabo, Largo, Fla.

[73] Assignee: Linvatec Corporation, Largo, Fla.

[21] Appl. No.: 919,875

[22] Filed: Jul. 27, 1992

[51] Int. Cl.⁵ .............................................. A61B 1/00
[52] U.S. Cl. .................................... 128/4; 206/303; 206/438; 359/510
[58] Field of Search ............... 128/4, 6; 604/163, 171, 604/172, 263; 359/507, 510, 511; 206/438, 303, 306, 802, 69

[56] References Cited

U.S. PATENT DOCUMENTS

| | | | |
|---|---|---|---|
| 3,536,192 | 10/1970 | Couper | 206/303 |
| 3,742,944 | 7/1973 | Sease . | |
| 4,041,942 | 8/1977 | Dougan et al. . | |
| 4,064,673 | 12/1977 | Gerigk et al. | 206/303 X |
| 4,185,625 | 1/1980 | Morris . | |
| 4,206,795 | 6/1980 | Regan | 206/303 X |
| 4,241,828 | 12/1980 | Bourdelle et al. | 206/802 X |
| 4,266,663 | 5/1981 | Geraci . | |
| 4,408,692 | 10/1983 | Sigel et al. . | |
| 4,691,702 | 9/1987 | Chantzis | 604/163 X |
| 4,767,409 | 8/1988 | Brooks . | |
| 4,817,592 | 4/1989 | Auchinleck et al. | 206/438 X |
| 4,886,049 | 12/1989 | Darras . | |
| 4,934,529 | 6/1990 | Richards et al. | 206/303 |
| 4,976,274 | 12/1990 | Hanssen . | |
| 5,061,246 | 10/1991 | Anapliotis . | |
| 5,078,483 | 1/1992 | Herzberg . | |
| 5,080,108 | 1/1992 | Roth . | |
| 5,149,326 | 9/1992 | Woodgrift et al. | 604/171 X |
| 5,168,863 | 12/1992 | Kurtzer | 128/4 |
| 5,198,894 | 3/1993 | Hicks | 128/4 X |
| 5,239,981 | 8/1993 | Anapliotis . | |

OTHER PUBLICATIONS

Two page excerpt from Microtek Medical, Inc., 1991 Catalog, Product No. 2904.

Primary Examiner—Richard J. Apley
Assistant Examiner—Karen A. Jalbert
Attorney, Agent, or Firm—Rosenblatt & Associates

[57] ABSTRACT

The present invention allows operating room personnel to easily and expeditiously drape an endoscope. The present invention is preferably made of polyethylene or some other suitable plastic material. The cylindrical drape cartridge itself acts as a shroud and functions as a sterile barrier. The drape cartridge consists of an inner and outer polyethylene tube which retains the polyethylene drape within its walls. The proximal end of the cartridge is mechanically secured by detents and a chamfer that encase a corrugated pattern of the polyethylene drape. The inner tube acts as a mandrel, allowing the drape to be compressed in a manner that accommodates the various lengths of required draping while lessening the bulk of the draping system.

23 Claims, 2 Drawing Sheets

ENDOSCOPIC DRAPING APPARATUS AND METHOD

FIELD OF THE INVENTION

This invention relates generally to the field of medical instruments and more particularly to an endoscopic draping system that is used to protect the camera head and the cable to prevent contamination during the endoscopic procedure.

BACKGROUND OF THE INVENTION

Surgeons are presently utilizing an endoscopic video system to access organs and biopsy sites that previously required more complex surgeries that entailed large incisions. The endoscopic procedures have become a preferable method of accessing the various procedural fields because the large open incisions traumatized surrounding tissue, increased the morbidity rate, and resulted in higher incidences of surgical complications. Complications are lessened by the endoscopic procedure, which results in shorter inpatient hospital stays. This in turn economically benefits the patients.

The endoscopic devices are comprised of an elongated tubular scope, a coupling mechanism that is attached to a camera head, a cable system, and the origin of power. A light source is introduced into the scope to allow visibility for videotaping. In order to maintain a sterile surgical field, the endoscopic device must be sterile or a portion of the scope, the coupling mechanism, the camera and the power source, must be draped by a sterile material. In the past the endoscopic devices, including the camera head and cables, were sterilized. Cables often became worn with repeated Cidex ® soakings. Seals deformed on the cable end fittings, jeopardizing the integrity of the joint. To counteract the wear and tear on expensive operating room equipment and to eliminate the need of costly repairs, cloth material drapes were utilized to prolong the equipment's life expectancy. Now, disposable drapes offer a more cost-effective means of maintaining a sterile barrier.

Surgeons typically use a 4-inch to 6-inch layflat disposal polyethylene tube layered drape. The drape will vary in thickness from 0.0015 inch to 0.003 inch, depending on the manufacturer and the scope that is to be draped. These drapes are pulled on both sides by two persons over the scope. The distal tip of the scope pierces the drape, and the remainder of the drape encases the endoscopic device. The fenestration in the drape near the scope head is hermetically sealed by surgical tape or rubber bands. The surgeons many times have difficulty in grasping the endoscopic device as the drape is loose and awkward.

U.S. Pat. No. 4,767,409 illustrates a catheter shield assembly which includes a front and rear hub, sized to permit the insertion of a catheter. A protective sleeve made of a clear plastic material is collapsed and permanently attached to the rear hub. This protective sleeve and the hub are supported by a clear, rigid, external plastic tube. The external support tube is connected to a front hub. This front hub is connected to a luer lock fitted to the catheter introducer which is inserted into the vein. The external support tubing is extended over the catheter to a position remote from the introducer. The problem with this catheter device is that the collapsible clear plastic tubing is permanently affixed to the front and rear hubs. The external support tubing cannot be disposed of prior to surgery. In fact, this external support is bulky and awkward. The problem with the collapsible plastic tubing is that sterile integrity cannot be maintained. The present invention protects the endoscopes against contaminants through use of the draping system. No external tubes are necessary for sterile protection. The draping cartridge is a disposable dispensing unit that eases application of the draping and is then removed from the procedural field. The cartridge allows substantial lengths of drape to be encapsulated into the cartridge tubing because of the corrugated method of packing the draping.

U.S. Pat. No. 5,078,483 demonstrates a sterile, disposable arthoscopic camera cover comprised of a disposable cover which encases tubular folded layers of film. The cover is formed of a disc-shaped sphere that encircles two elongated tubular walls that contain the longitudinal tubular draping. The arthroscopic cover utilizes longitudinal elongated tubing to encase the scope, whereas the present invention simply contains a corrugated method of packing the drape. The present invention is easier to use, is less time-consuming, and is less complex in its construction.

Accordingly, one of the objects of the present invention is to ease the draping process of the endoscopic equipment. This objective is accomplished by a compressed dispensing shroud. The polyethylene drape is encased within the draping cartridge (the dispensing shroud) so that one person can easily spread the draping material over the endoscopic and achieve an impervious fit.

SUMMARY OF THE INVENTION

The present invention allows operating room personnel to easily and expeditiously drape an endoscope. The present invention is preferably made of polyethylene or some other suitable plastic material. The cylindrical drape cartridge itself acts as a shroud and functions as a sterile barrier. The drape cartridge consists of an inner and outer polyethylene tube which retains the polyethylene drape within its walls. The proximal end of the cartridge is mechanically secured by detents and a chamfer that encase a corrugated pattern of the polyethylene drape. The inner tube acts as a mandrel, allowing the drape to be compressed in a manner that accommodates the various lengths of required draping while lessening the bulk of the draping system. The inner tube additionally supports the corrugated pattern of draping. This structural support permits the manufacturer to lessen the diameter of the polyethylene drape that lies within the outer and inner tubes. The finer polyethylene drape results in a smaller mass of plastic that achieves a streamlined conformed fit to the rear of the endoscope. This eliminates the need for operating personnel to tape and rubberband the loose, hanging plastic material that plagued prior draping systems. The conformed streamlined fit assures the surgeon greater maneuverability, less bulk, and eliminates slippage.

The drape cartridge forms a cylindrical polyethylene tube which provides the necessary clearance to accommodate the camera head and the cartridge coupling system. A fold of the polyethylene drape extends beyond the distal end of the drape cartridge. An expandable fenestration lies in the center of the fold for a secure, impervious fit around the head of the scope. The drape cartridge and the fenestration engage the scope into the cartridge coupler to fasten the drape at the distal end of the scope. The drape cartridge functions as a grasping device. The cartridge allows a smooth and easy dispersement of the drape over the endoscope from the distal end of the drape cartridge. The polyethylene drape is secured within the walls of the outer and inner tubes. The outer and inner shells at the proximal end of the drape cartridge assure that the corrugated draping is secured within the outer and inner tubes. The operating room personnel with one hand can pull the drape cartridge over the camera cable. By holding onto the camera head, the other hand dispenses the drape to attain the desirable coverage.

DETAILED DESCRIPTION OF THE PREFERRED EMBODIMENT

Figure 2:
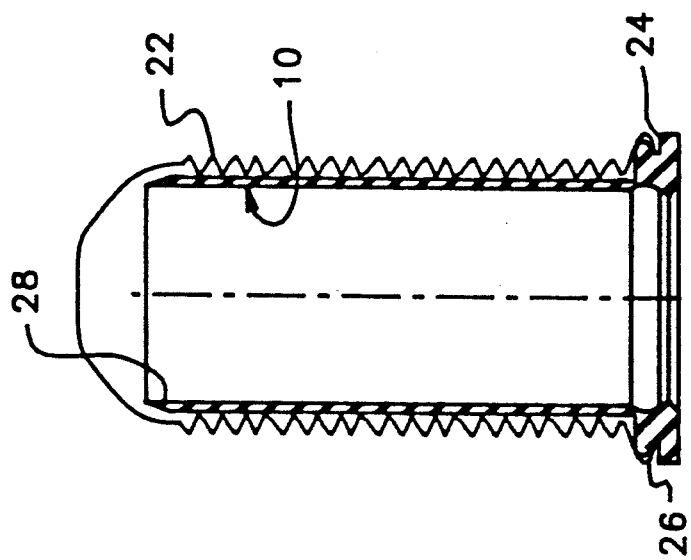
FIG. 2 is a sectional elevational view of a portion of the dispenser showing how the drape is packed onto the dispenser.
Figure 1:
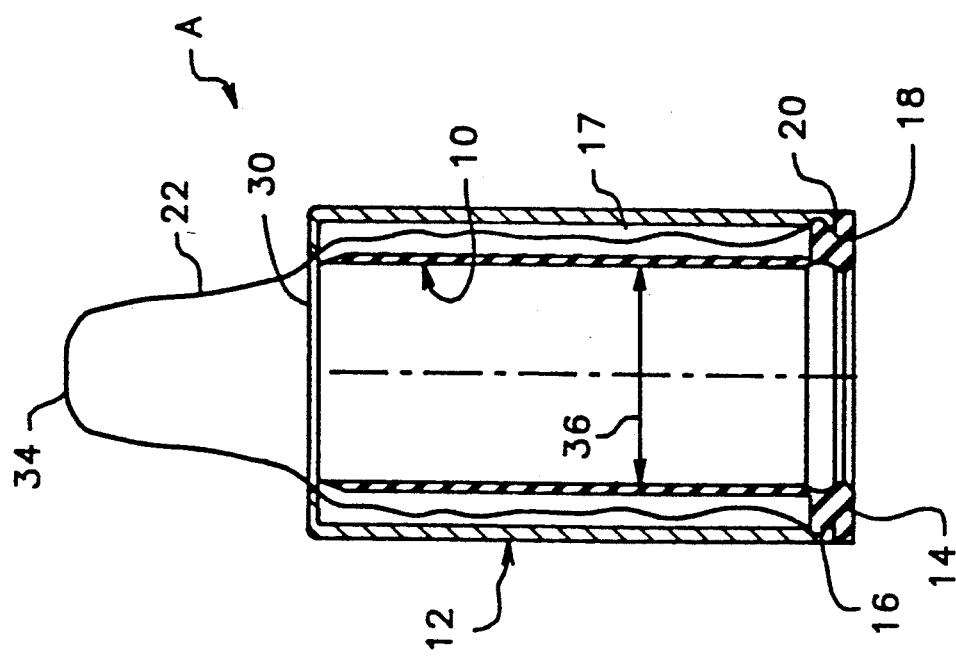
FIG. 1 is a sectional elevational view showing the dispenser and drape of the present invention.

The apparatus A is shown in FIG. 1. The apparatus is made of two principal components, an inner shell 10 and an outer shell 12. Inner shell 10 has a principally tubular configuration, having a flange 14 at one end thereof. Flange 14 has a detent 16 which facilitates engagement of the outer shell 12 to the inner shell 10 by virtue of annular ring 18, which is found at the end 20 of outer shell 12. A drape 22 is initially mounted to inner shell 10, as shown in FIG. 2. The edge 24 of drape 22 is inserted into peripheral groove 26. Whereupon when the annular ring 18 of the outer shell 12 is inserted into groove 26, the edge 24 of drape 22 is secured to inner shell 10. Alternatively, the edge 24 of drape 22 can be extended beyond groove 26. Similarly, when the outer shell 12 is fitted over the inner shell 10 and ring 18 extends into groove 26, the drape 22 will be secured to the apparatus A. The method of securing edge 24 can vary without departing from the spirit of the invention. For example, a 7½-ft long drape can be installed over inner shell 10 which may be only about 3 inches long. The ratio of the expanded length to stored length can be greater than 10:1 and in the example above, about 30:1. The annulus 17 between inner body 10 and outer body 12 has a low profile of only about 0.2-inch radial clearance. Drape 22 is thus short folded with folds of less than about ¼-inch in length, as shown in FIG. 2, to allow it to fit in such narrow radial clearance. The use of a low clearance in annular passage 17 facilitates one-handed usage of apparatus A by reducing its outside dimension. Further, the cylindrical shape of drape 22 eliminates much excess volume in prior drapes which required excess taping to keep such drape material out of the surgeon's way.

To prevent snagging or tearing of the drape 22 as it is dispensed, the edge 28 of the inner shell 10 is tapered, preferably 20° from the longitudinal axis. Those skilled in the art can readily appreciate that the inner shell 10 acts as a mandrel over which to corrugate the drape 22 so that a significant length of drape 22 can be compressed in a relatively small space circumscribing inner shell 10.

Referring to FIG. 1, it can be seen that outer shell 12 has an opening 30 which is in alignment with inner shell 10, creating an exit passageway 32 through which drape 22 feeds out as the combination of the inner and outer shells 10 and 12, respectively, are advanced over the components to be protected.

Figure 3:
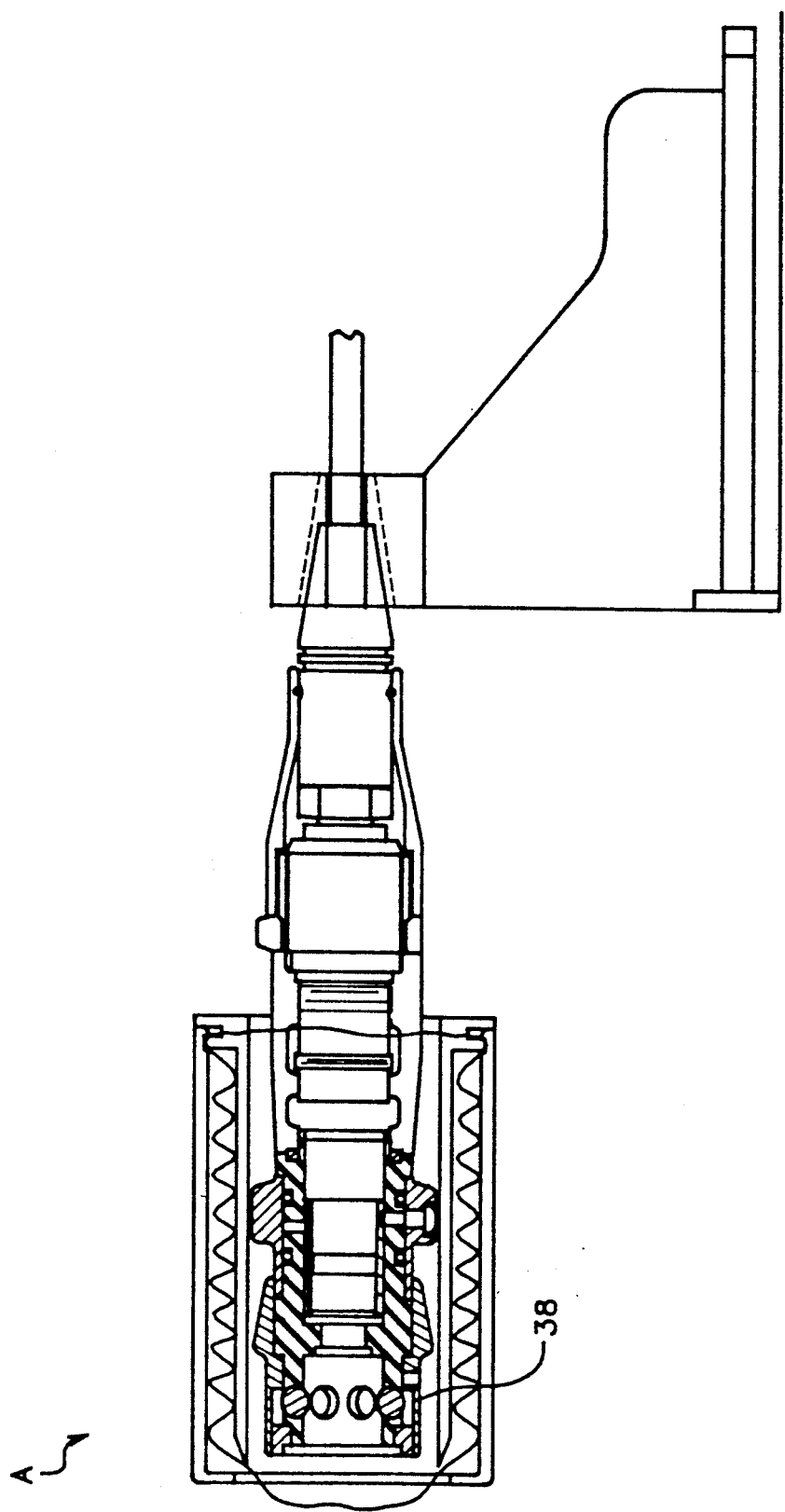
FIG. 3 is a sectional elevational view showing how the dispenser is used to drape a coupling on an endoscopic assembly.

The drape 22 has an opening 34 which is selectively sized to become engaged on the equipment to be draped. Depending on the point of contact of the drape 22 over the equipment, the size of the opening 34 may be varied. One way to install the drape 22 is over a coupling, as shown in FIG. 3. In FIG. 3, the female part of the coupling is illustrated, with the apparatus A fitted over the coupling as it is advanced over the remainder of the coupling and the camera attached thereto. It should be noted that the apparatus of the present invention is applicable over any device which needs to be isolated for the purposes of sterilization. The limiting factor is the clearance represented by arrow 36 in FIG. 1. Once the clearance 36 exceeds the profile of the object to be isolated, the apparatus A, grasped by a surgeon or other operating room personnel, can be advanced with one hand over the object to be covered. The engagement of the drape 22 to the object stops the progress of the end of drape 22 at opening 34. Thereafter, further advancement of inner shell 10 and outer shell 12 results in feeding out of the drape 22 through passageway 32. The operation can be one-handed. Significantly greater volumes of draped area can be accommodated due to the unique manner of packing the drape 22 around the inner shell 10, as illustrated in FIG. 2. Additionally, the shape of the drape 22 can more readily accommodate the shape of the object being draped without significant amounts of slack which has resulted from prior art folding arrangements. The excess slack in the past has required additional taping and rubber banding to avoid a bulky drape getting in the way of the surgeon or other operating room personnel.

Those skilled in the art can appreciate that the opening 34 can be sized so that the drape 22 covers the entire coupling and not only the female component 38, as shown in FIG. 3. In such embodiments, the drape 22 would fit over the scope as well as the lateral opening for a light source typically mounted to such scopes. A wide variety of clearances 36 can be employed in the apparatus to accommodate instruments of varying size. Additionally, different lengths of drapes can be accommodated in the apparatus A by varying its length. With proper sterilization, the apparatus A can be reused if desired. The snap fit of the outer shell 12 to the inner shell 10 offers a secure grip on the drape 22 as it is being advanced over the objects to be shielded.

The foregoing disclosure and description of the invention are illustrative and explanatory thereof, and various changes in the size, shape and materials, as well as in the details of the illustrated construction, may be made without departing from the spirit of the invention.

I claim:

1. A method of draping an endoscopic instrument, comprising:
   mounting a drape over a mandrel;
   securing a leading end of said drape to the mandrel;
   moving a bore extending through said mandrel over the instrument;
   engaging the instrument with a trailing end of said drape;
   beginning to feed said drape off said mandrel and around the instrument by continuation of said moving after said engaging.

2. The method of claim 1, comprising:

moving an opening on the drape over the instrument prior to said engagement step.

3. The method of claim 2, wherein said mounting step further comprises:
short folding said drape over said mandrel.

4. The method of claim 3, wherein said securing step further comprises:
mounting an outer housing over said mandrel;
securing said drape to said mandrel by contact of said outer housing to the mandrel.

5. The method of claim 4, further comprising:
providing a passageway between said mandrel outside of said bore and said outer housing to allow said drape to cover the instrument as said drape begins to feed off said mandrel.

6. The method of claim 5, further comprising:
tapering said mandrel adjacent said passageway to facilitate said feeding step.

7. The method of claim 4, wherein said securing step further comprises:
trapping said leading end between a snap fit of said outer housing to said mandrel;
storing said drape in an annular space between said mandrel and said outer housing until said beginning to feed step draws said drape through said passageway.

8. The method of claim 7, further comprising:
providing an opening in the trailing end of said drape;
slipping said drape over the instrument with a portion of the instrument to be draped extending through said opening.

9. The method of claim 8, further comprising:
slipping said drape over the endoscopic instrument by advancing said opening over the instrument;
covering with said drape the endoscopic instrument comprising at least one of a camera, a coupling, and a light source.

10. The method of claim 9, wherein:
slipping said drape over a coupling connecting the endoscopic instrument to a camera;
securing said drape in said coupling by putting the coupling together, with said opening on said coupling;
covering a camera and a portion of the coupling with said drape;
leaving undraped the remainder of the coupling, the light source, and the endoscopic instrument.

11. The method of claim 1, further comprising:
providing an opening in the trailing end of said drape;
slipping said drape over the instrument with a portion of the article not to be draped extending through said opening.

12. The method of claim 11, further comprising:
slipping said drape over the endoscopic instrument by advancing said opening over the instrument;
covering with said drape the endoscopic instrument comprising at least one of a camera, a coupling, and a light source.

13. The method of claim 11, wherein:
slipping said drape over a coupling connecting the endoscopic instrument to a camera;
securing said drape in said coupling by putting the coupling together, with said opening on said coupling;
covering a camera and a portion of the coupling with said drape;
leaving undraped the remainder of the coupling, the light source, and the endoscopic instrument.

14. In combination, an endoscopic instrument comprising at least one of a camera, a coupling, or a light source, and an apparatus for dispensing a drape around said endoscopic instrument, said apparatus comprising:
a mandrel having a bore therethrough, said bore being larger than said instrument to allow said mandrel to pass over said instrument;
a drape mounted to said mandrel;
an outer assembly mounted to said mandrel creating an annular space in which said drape is disposed, said outer assembly having an opening thereon;
said drape extending into said bore such that advancement of said outer assembly brings said drape into contact with said instrument, with further movement of said outer assembly resulting in said drape extending through said opening in said outer assembly to drape said instrument as said bore is passed over said instrument.

15. The apparatus of claim 14, wherein:
said drape is corrugated on said mandrel to allow a given length of drape, when expanded, to be housed in said annulus on a mandrel that is significantly shorter than its expanded length.

16. The apparatus of claim 15, wherein:
the ratio of said drape length when mounted over the said instrument and said drape when mounted on said mandrel is greater than 10:1.

17. The apparatus of claim 16, wherein said drape is folded in folds not exceeding 0.5 inch.

18. The apparatus of claim 14, wherein:
said outer assembly snap fits to said mandrel;
said snap fit engaging one end of said drape to retain it as its opposite end is fed out through said opening.

19. The apparatus of claim 14, wherein:
said drape has an opening, said opening straddling the said instrument to be draped;
said drape is cylindrically shaped when extended over the said instrument;
said bore in said mandrel sized to fit closely over the said instrument such that said drape covers the said instrument with a minimum of slack.

20. In combination a drape dispenser and an endoscopic instrument comprising at least one of a camera, a coupling, or a light source, said dispenser comprising:
a mandrel having a bore therethrough, said bore being larger than said instrument to allow said mandrel to pass over said instrument;
a cover connected to said mandrel having an opening adjacent said bore to define an annular space for storage of a drape and an exit passageway from said annulus through said opening;
means for securing an end of a drape in said annulus;
said cover adapted to be grasped with one hand in applying a drape over said instrument by moving said bore over said instrument.

21. The dispenser of claim 20, further comprising:
a drape mounted to said mandrel in a manner where its mounted length is at most 1/10 of its extended length when draped over the instrument.

22. The dispenser of claim 21, wherein:
said drape has a generally cylindrical shape when extended over the instrument, thereby closely conforming to the instrument over which said bore in said mandrel has been passed.

23. A drape dispenser allowing one person to drape an instrument for isolation thereof, said dispenser comprising:

a mandrel having a first end and a second end and a bore therethrough, said bore being larger than the instrument to allow said mandrel to pass over the instrument, said mandrel having a flange at said first end;

a drape mounted to said mandrel, a leading end of said drape secured to said first end of said mandrel and a trailing end of said drape having an expandable fenestration for imperviously contacting the instrument to be draped;

a cover connected to said mandrel at said flange, capturing one end of said drape between said flange and said cover, and having an opening adjacent said bore at said second end of said mandrel to define an annular space for storage of said drape and an exit passageway from said annulus through said opening;

said cover adapted to be grasped with one hand in applying said drape over the instrument by engaging the expandable fenestration of said drape with the instrument and feeding said drape off said mandrel by moving said bore over the instrument.

* * * * *